United States Patent
Ishikawa et al.

(10) Patent No.: US 7,150,862 B2
(45) Date of Patent: Dec. 19, 2006

(54) METHOD OF MANUFACTURING POWDER

(75) Inventors: Tsuyoshi Ishikawa, Tokyo (JP);
Masanori Nakasu, Tokyo (JP);
Takatoshi Kudou, Tochigi (JP);
Yoshiyuki Ogawara, Tochigi (JP);
Tsutomu Takahashi, Tochigi (JP);
Katsumi Kawamura, Tokyo (JP)

(73) Assignee: PENTAX Corporation, Tokyo (JP)

(*) Notice: Subject to any disclaimer, the term of this patent is extended or adjusted under 35 U.S.C. 154(b) by 273 days.

(21) Appl. No.: 10/339,302

(22) Filed: Jan. 10, 2003

(65) Prior Publication Data

US 2003/0214062 A1 Nov. 20, 2003

(30) Foreign Application Priority Data

Jan. 11, 2002 (JP) ............................ 2002-004596

(51) Int. Cl.
| | |
|---|---|
| *C01B 25/32* | (2006.01) |
| *C01B 21/072* | (2006.01) |
| *C01B 21/076* | (2006.01) |
| *C01B 21/064* | (2006.01) |
| *C01B 21/068* | (2006.01) |
| *C01G 23/00* | (2006.01) |
| *C01G 25/02* | (2006.01) |

(52) U.S. Cl. ..................... 423/308; 423/263; 423/290; 423/309; 423/339; 423/344; 423/411; 423/412; 423/440; 423/448; 423/598; 423/608; 423/610; 423/625; 423/626; 423/659

(58) Field of Classification Search ................ 423/308, 423/309, 311, 263, 290, 339, 344, 411, 412, 423/440, 448, 598, 608, 610, 625, 626, 659

See application file for complete search history.

(56) References Cited

FOREIGN PATENT DOCUMENTS

| EP | 0943643 | 9/1999 |
|---|---|---|
| EP | 943643 | 9/1999 |
| JP | 52-76324 | 6/1977 |
| JP | 59152224 | 8/1984 |
| JP | 7-102006 | 4/1995 |

(Continued)

OTHER PUBLICATIONS

Database WPI, Section Ch, Week 197732, Derwent Publications Ltd., London, GB; Class Lo2, An 1977-56419Y, XP002263821, (no date).

(Continued)

*Primary Examiner*—Wayne A. Langel
(74) *Attorney, Agent, or Firm*—Greenblum & Bernstein, P.L.C.

(57) ABSTRACT

A method of manufacturing a powder, by which it is possible to adjust the strength of the obtained powder is provided. The manufacturing method of a powder involves a step of preparing a slurry containing agglomerated particles of a synthetic material which is produced by reacting a first material and a second material under agitation, and a step of drying the slurry to obtain a powder of the synthetic material. The method has a feature that the particle size of the agglomerated particles is adjusted by, in the step of preparing a slurry, controlling agitation power for agitating the slurry. In the step of preparing a slurry, it is preferable that the slurry is initially agitated at a first agitation power, and at the time when the viscosity of the slurry approaches its maximum value, or at the time when the pH value of the slurry reaches the vicinity of the isoelectric point of the synthetic material, the agitation power is lowered from the first agitation power to a second agitation power. Further, it is preferable that before or after the completion of the reaction of the first material and the second material, the agitation power is increased from the second agitation power to a third agitation power.

25 Claims, 1 Drawing Sheet

FOREIGN PATENT DOCUMENTS

JP       07102006       4/1995

OTHER PUBLICATIONS

Database WPI, Section Ch, Week 199524, Derwent Publications Ltd., London, GB; Class A18, An 1995-182991, XP002263822, (no date).

Patent Abstracts of Japan, vol. 008, No. 283 (C-258), Dec. 25, 1994.

M. Giulietti et al., "Industrial Crystallization and Precipitation from solutions: State of the Technique", Brazilian Journal of Chemical Engineering, vol. 18, No. 4, 2001; print ISSN 0104-6632, (no month).

English Language Abstract of JP Appln. No. 7-102006, (no date).

English Language Abstract of JP Appln. No. 52-76324, (no date).

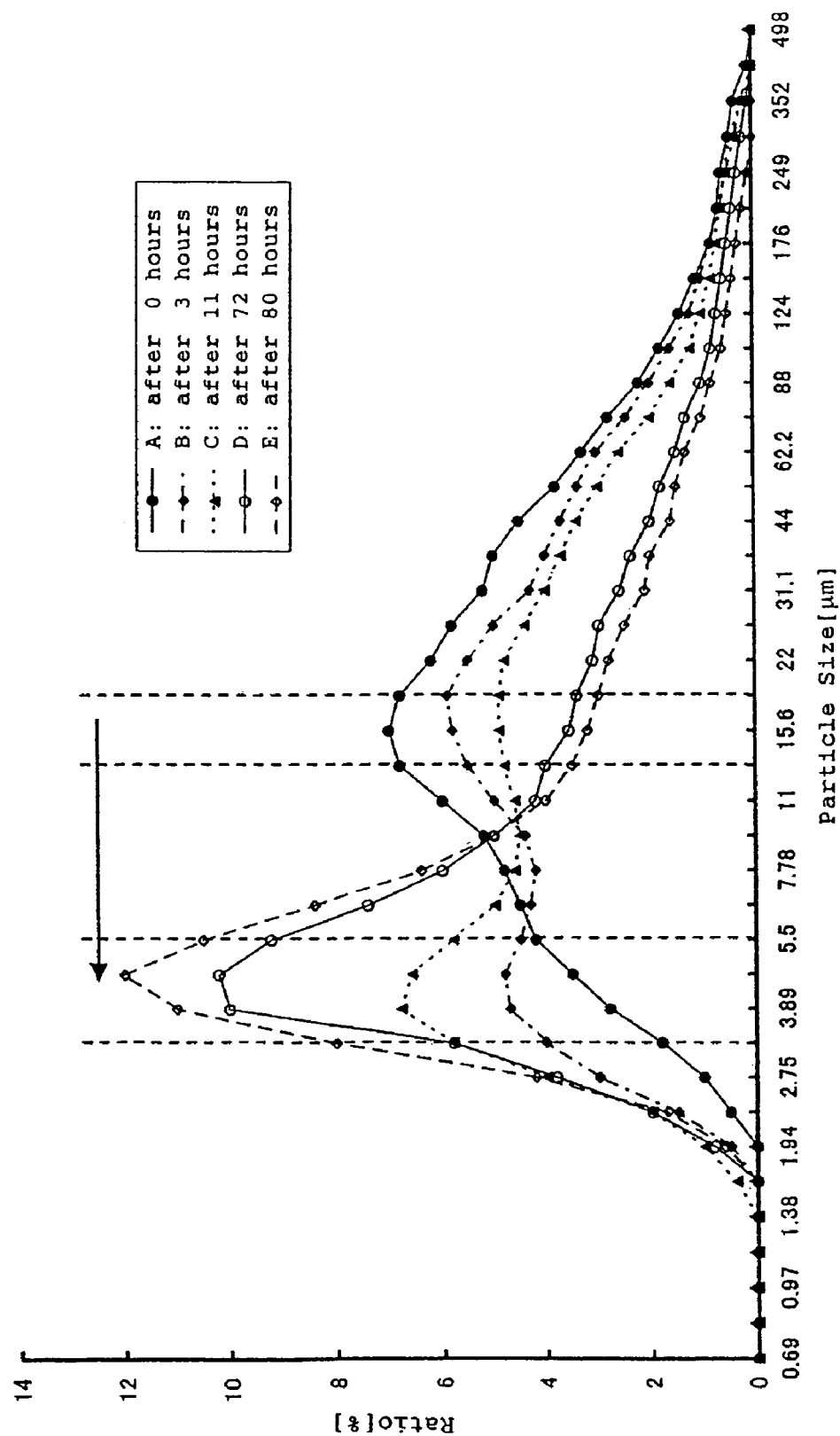

METHOD OF MANUFACTURING POWDER

BACKGROUND OF THE INVENTION

1. Field of the Invention

This invention relates to a method of manufacturing a powder.

2. Description of the Prior Art

A calcium phosphate-based compound, a kind of ceramic material, is widely used as, for example, a biomaterial and a stationary phase material for chromatography.

In using a calcium phosphate-based compound as a biomaterial, a powder of calcium phosphate-based compound is prepared from a slurry containing the calcium phosphate-based compound. The prepared powder is formed into a desired shape to obtain a green body, and it is then sintered. The thus obtained sintered body is used for artificial bones, dental implants and the like in the medical and dental fields.

In using a calcium phosphate-based compound as a stationary phase material for chromatography, a calcium phosphate-based compound powder is prepared in the same manner as in the case for a biomaterial. The thus prepared powder is sintered, and the sintered powder is used as a stationary phase to be filled in a column or the like for chromatography.

A problem exists, however, with such a sintered body for use in artificial bones, dental implants, and the like in that processing and control of porosity are difficult to carry out if the prepared powder does not have sufficient (uniform) particle strength. Generally, such a sintered body is manufactured through the following three steps. Firstly, a prepared powder is pre-sintered and then ground using a grinder. Secondly, the ground powder is mixed with, for example, an aqueous solution of methylcellulose. Thirdly, the mixture is gelled to be formed into a block shape. The grinding of the pre-sintered powder in the first step is necessary for properly giving irregularities on the surface of each particle of the ground powder so that each particle can have an increased surface area, thereby increasing contact area between the particles. A sintered body manufactured from such a powder of which particles have increased surface area exhibits excellent mechanical strength. However, if the particle strength of the prepared powder (that is a powder prior to pre-sintering) is too low, the pre-sintered powder is excessively fragmented to become too fine particles when ground. On the other hand, if the particle strength of the prepared powder is too high, such an effect due to grinding as described above can not be obtained so that the ground powder will not have a uniform particle size distribution, and thus a sintered body manufactured from such a powder can not have uniform porosity and strength.

A problem also exists with a sintered powder for use as a stationary phase for chromatography in that if a powder prepared prior to sintering does not have sufficient particle strength, the sintered powder will tend to collapse when filled in a column, which may result in clogging of a filter. One outcome of this problem is that proper separation of proteins can not be carried out.

SUMMARY OF THE INVENTION

To solve the problems described above, the inventors have conducted extensive research and, as a result, have found that in a step of preparing a slurry containing a synthetic material such as a calcium phosphate-based compound, by adjusting the particle size of agglomerated particles of the synthetic material existing in the slurry, it is possible to adjust the strength of the obtained powder to one desired.

It is therefore an object of the present invention to provide a method of manufacturing a powder, by which it is possible to adjust the strength (particle strength) of the obtained powder.

In order to achieve the object mentioned above, the present invention is directed to a method of manufacturing a powder. The method comprises the steps of preparing a slurry containing agglomerated particles of a synthetic material which is produced by reacting a first material and a second material under agitation, and drying the slurry to obtain a powder of the synthetic material, wherein the particle size of the agglomerated particles is adjusted by, in the step of preparing a slurry, controlling an agitation power for agitating the slurry. With this method, it is possible to adjust the strength of the obtained powder. It is to be noted here that "agitation power" is referred to an electrical power (wattage level) which is applied for agitating a slurry.

In the method described above, it is preferred that the agitation power is controlled on the basis of a change in the viscosity of the slurry and/or a change in the pH value of the slurry. In this way, the agitation power can be controlled easily and reliably.

In this case, the agitation power preferably includes at least a first agitation power and a second agitation power which is lower than the first agitation power.

Further, in the case that the control of the agitation power is carried out on the basis of a change in the viscosity of the slurry, it is preferred that the slurry is initially agitated at the first agitation power, and at the time when the viscosity of the slurry approaches its maximum value, the slurry is agitated at the second agitation power. On the other hand, in the case that the control of the agitation power is carried out on the basis of a change in the pH value of the slurry, it is preferred that the slurry is initially agitated at the first agitation power, and at the time when the pH value of the slurry reaches the vicinity of the isoelectric point of the synthetic material, the slurry is agitated at the second agitation power. This enables the strength of the obtained powder to be precisely adjusted.

In this case, the first agitation power is preferably an output of 0.75 to 2 W for 1 L of the slurry, by which it is possible to further increase the efficiency of the reaction of the first material and the second material, and the second agitation power is preferably an output of 0.27 to 0.7 W for 1 L of the slurry, by which it is possible to further increase the efficiency of the agglomeration of the synthetic material.

Furthermore, the agitation power preferably includes a third agitation power which is larger than the second agitation power, in which the control of the agitation power is carried out so that the slurry is agitated at the third agitation power before or after the reaction of the first material and the second material is completed. This enables the particle size of agglomerated particles of the synthetic material existing in the slurry to be efficiently adjusted.

In this case, the third agitation power is preferably an output of 0.75 to 2 W for 1 L of the slurry, by which it is possible to more efficiently adjust the particle size of agglomerated particles of the synthetic material existing in the slurry.

Further, a duration of agitation of the slurry at the third agitation power (hereinafter, simply referred to as a "duration of agitation at the third agitation power") is preferably determined on the basis of a particle size distribution of the agglomerated particles. In this way, the duration of agitation at the third agitation power can be more precisely determined.

In this case, the duration of agitation at the third agitation power is preferably controlled so that the ratio of agglomerated particles having a particle size of one-half of or less than a target particle size of the powder to the total of the agglomerated particles existing in the slurry is 55% or more. Also, the duration of agitation at the third agitation power may be controlled so that agglomerated particles having a particle size of one-thirds of or less than a target particle size of the powder occupy the largest percentage of the total of the agglomerated particles existing in the slurry. In this way, it is possible to further enhance the strength of the obtained powder.

In the present invention, at least one of the first material and the second material is preferably used in a solution form, which enables the synthetic material to be produced more easily and efficiently.

Further, the synthetic material is preferably a ceramic material, and more preferably a calcium phosphate-based compound.

Furthermore, it is preferred that the first material, the second material and the synthetic material are calcium hydroxide, phosphoric acid and hydroxyapatite, respectively.

The present invention is suitable for manufacturing a powder of a ceramic material, especially a powder of hydroxyapatite which is a kind of calcium phosphate-based compound.

In this case, the completion of the reaction of the calcium hydroxide and the phosphoric acid is preferably determined by detecting an amount of a substance other than the hydroxyapatite existing in the slurry, by which it is possible to precisely determine the completion of production of hydroxyapatite.

Further, the substance is preferably calcium hydroxide or tricalcium phosphate. By detecting an amount of such a substance, it is possible to more precisely determine the completion of production of hydroxyapatite.

Furthermore, in a case that a target particle size of the powder is set to be 15 to 43 μm, the duration of agitation at the third agitation power is preferably controlled so that the ratio of agglomerated particles having a particle size of one-half of or less than a target particle size of the powder to the total of the agglomerated particles existing in the slurry is 55% or more. Also, in a case that a target particle size of the powder is set to be 15 to 43 μm, the duration of agitation at the third agitation power may be controlled so that agglomerated particles having a particle size of one-thirds of or less than a target particle size of the powder occupy the largest percentage of the total of the agglomerated particles existing in the slurry. In this way, it is possible to further enhance the strength of the obtained powder.

Moreover, when the ratio of agglomerated particles having a particle size of 13.0 to 18.5 μm is defined as A, and the ratio of agglomerated particles having a particle size of 3.27 to 5.50 μm is defined as B, the duration of agitation at the third agitation power is preferably controlled based on the ratio between the A and B. This makes it possible to more precisely determine the duration of agitation at the third agitation power.

In this case, the duration of agitation at the third agitation power is preferably controlled so that the ratio between the A and B satisfies the formula of B/A>2, by which it is possible to further enhance the strength of the obtained hydroxyapatite powder.

BRIEF DESCRIPTION OF THE DRAWING

The sole FIGURE is a graph which shows the particle size distribution of agglomerated particles of hydroxyapatite existing in a slurry depending on the difference in the duration of agitation at a third agitation power.

DETAILED DESCRIPTION OF THE INVENTION

Hereinbelow, a detailed description will be made with regard to a manufacturing method of a powder according to the present invention with reference to a preferred embodiment.

The manufacturing method of a powder of the present invention involves a step of preparing a slurry containing agglomerated particles of a synthetic material which is produced by reacting a first material and a second material under agitation, and a step of drying the slurry to obtain a powder of the synthetic material.

In this regard, it is to be noted that in this specification the word "powder" has a broad meaning that includes powder particles, granules and the like, and a shape or form thereof is not particularly limited.

In the present invention, the synthetic material may be either of an organic material or an inorganic material, but an inorganic material, especially a ceramic material is preferred.

Examples of the ceramic material include: oxide ceramics such as alumina, silica, titania, zirconia, and yttria; calcium phosphate-based compounds; nitride ceramics such as silicon nitride, aluminum nitride, titanium nitride, and boron nitride; carbide ceramics such as graphite and tungsten carbide; and ferroelectric materials such as barium titanate, strontium titanate, PZT, PLZT, and PLLZT, and the like.

Among these ceramic materials, calcium phosphate-based compounds are used as, for example, a biomaterial and a stationary phase material for chromatography. Examples of such calcium phosphate-based compounds include: apatites such as hydroxyapatite, fluorapatite, and carbonate apatite; dicalcium phosphate; tricalcium phosphate; tetracalcium phosphate; and octacalcium phosphate.

Among these calcium phosphate-based compounds, hydroxyapatite has good biocompatibility, and is therefore used in the medical and dental fields as a biomaterial for use in manufacturing a filler, artificial bones, and dental implants. In addition, hydroxyapatite has, for example, excellent protein-adsorption properties.

In the present embodiment, an explanation will be given using hydroxyapatite as the representative of the synthetic material of the present invention. Needless to say, the synthetic material of the present invention is not limited thereto.

The manufacturing method of a powder of the present embodiment involves a step of preparing a slurry containing agglomerated particles of hydroxyapatite (this step is referred to as "S1"), and a step of drying the slurry to obtain a powder of hydroxyapatite (this step is referred to as "S2"). Hereinbelow, these steps will be described in order.

<S1: Step of Preparing Slurry Containing Agglomerated Particles of Hydroxyapatite>

In this step, to prepare a slurry containing agglomerated particles of hydroxyapatite, calcium hydroxide (a first material) and phosphoric acid (a second material) are reacted under agitation.

<S11>

First, an aqueous solution of phosphoric acid (second material) is dropped into a slurry containing calcium hydroxide (first material) placed in a container (not shown) with the slurry in the container being agitated at a first agitation power to mix the aqueous solution of phosphoric acid and the slurry containing calcium hydroxide.

The present embodiment uses a wet method in which phosphoric acid (second material) is used as an aqueous solution. By this method, it is possible to produce hydroxyapatite (synthetic material) more easily and efficiently without the need for costly equipment for manufacturing.

In this regard, it is to be noted that in the present invention it is sufficient that at least one of the first and second materials is used in a solution form. Of course, both the materials may be used in a solution form.

Furthermore, the agitation facilitates the reaction of calcium hydroxide and phosphoric acid, that is, the agitation increases the efficiency of the reaction of calcium hydroxide and phosphoric acid.

The first agitation power is not limited to any specific value, but is preferably an output of about 0.75 to 2 W, and more preferably an output of about 0.925 to 1.85 W, for 1 L of the slurry. By setting the first agitation power to within the above range, it is possible to further increase the efficiency of the reaction of calcium hydroxide and phosphoric acid.

As the reaction of calcium hydroxide and phosphoric acid gradually proceeds, fine particles of hydroxyapatite (synthetic material) (hereinafter, simply referred to as "fine particles") are produced in the slurry. In the slurry, some of the fine particles are positively charged and others are negatively charged, so that a van der waals force (intermolecular force) acts between the positively charged fine particles and the negatively charged fine particles, thereby the agglomeration of the fine particles occurs. In this way, agglomerated particles of hydroxyapatite (synthetic material) (hereinafter, simply referred to as "agglomerated particles") are produced. As the production of the agglomerated particles proceeds, the viscosity of the slurry gradually increases.

As the reaction of calcium hydroxide and phosphoric acid further proceeds, the ratio of positive charges to negative charges in the slurry becomes close to each other. Thus a repulsive force acting between the fine particles decreases, whereby the agglomeration of the fine particles is accelerated. As a result, the viscosity of the slurry sharply rises to approach its maximum value (peak value).

In this regard, it is to be noted that, even in a case that a synthetic material other than hydroxyapatite is to be produced, such a sharp rise in the viscosity of a slurry generally occurs at the time when the pH value of the slurry reaches the vicinity of the isoelectric point of the synthetic material.

<S12>

Next, when the viscosity of the slurry approaches its maximum value, the agitation power for the slurry is changed to a second agitation power that is lower than the first agitation power. By controlling the agitation power in this way, it is possible to facilitate reaction (synthesis) of calcium hydroxide (first material) and phosphoric acid (second material) without affecting the agglomeration of the fine particles.

Namely, in this embodiment, the agitation power is controlled based on a change in the viscosity of the slurry. This makes it possible to carry out the control of the agitation power easily and reliably since the viscosity of the slurry can be easily measured.

It is to be noted here that the second agitation power is preferably set at a level that does not reduce the efficiency of the reaction of calcium hydroxide and phosphoric acid.

The second agitation power is not limited to any specific value, but is preferably an output of about 0.27 to 0.7 W, and more preferably an output of about 0.37 to 0.555 W, for 1 L of the slurry. By setting the second agitation power to within the above range, it is possible to facilitate reaction (synthesis) of calcium hydroxide and phosphoric acid without affecting the agglomeration of the fine particles.

The agitation of the slurry at the second agitation power is continued with checking of the progress of the reaction of calcium hydroxide and phosphoric acid, that is, with checking of the progress of production of hydroxyapatite.

In this regard, it is to be noted that, in a case that synthesis of hydroxyapatite has not yet been completed, the existence of calcium hydroxide (unreacted substance) is recognized in the slurry. On the other hand, in a case that synthesis of hydroxyapatite has been fully completed, the existence of a secondary product such as tricalcium phosphate or the like is recognized in the slurry.

Therefore, by detecting an amount of a substance other than hydroxyapatite (e.g., calcium hydroxide, tricalcium phosphate or the like) existing in the slurry, it is possible to precisely determine whether or not synthesis of hydroxyapatite has been completed.

It is to be noted that detection of calcium hydroxide, tricalcium phosphate and the like existing in the slurry can be carried out by subjecting a sampled and dried slurry to X-ray diffraction.

As described above, since a sharp rise in the viscosity of the slurry generally occurs at the time when the pH value of the slurry reaches the vicinity of the isoelectric point of the synthetic material, the agitation power for the slurry may also be lowered (changed) from the first agitation power to the second agitation power at this timing. Namely, control of the agitation power may be performed based on a change in the pH value of the slurry instead of a change in the viscosity of the slurry.

In a case of a synthetic material in which a change in the viscosity of a slurry and a change in the pH value of a slurry do not occur at the same timing, control of the agitation power may be selectively performed on the basis of either a change in the viscosity of the slurry or a change in the pH value of the slurry depending on the kind of the synthetic material.

Further, control of the agitation power may be performed on the basis of both a change in the viscosity of the slurry and a change in the pH value of the slurry, as required.

The secondary agitation (S12) described above need not be employed if an obtained powder simply requires increased strength.

<S13>

Next, after the determination that the reaction of calcium hydroxide and phosphoric acid is almost or fully completed, that is, before or after the completion of the reaction, the agitation power for the slurry is changed from the second agitation power to a third agitation power that is higher than the second agitation power. The agitation by this third agitation power makes it possible to break (crush) agglomerated particles having relatively large particle sizes which exist in the slurry, and to thereby obtain agglomerated particles having relatively small particle sizes.

the sole FIGURE shows the particle size distribution of agglomerated particles of a synthetic material existing in the slurry wherein the synthetic material is hydroxyapatite.

Specifically, the sole FIGURE is a graph which shows the particle size distribution of agglomerated particles of hydroxyapatite existing in the slurry depending on the difference of the duration of agitation at the third agitation power.

As shown by the curve A in the sole FIGURE, the particle size distribution of agglomerated particles existing in the slurry at the time of the completion of the step S12 described above shows a normal distribution, in which agglomerated particles having a particle size of about 16.0 µm mainly exist.

As the duration of agitation at the third agitation power becomes long, agglomerated particles having a particle size of 13.0 to 18.5 µm decrease, while agglomerated particles having a particle size of 3.27 to 5.50 µm increase, as shown by the curves B to E in the sole FIGURE.

The third agitation power is not limited to any specific value, but is preferably an output of about 0.75 to 2 W, and more preferably an output of about 0.925 to 1.85 W. By setting the third agitation power to within the above range, it is possible to more efficiently adjust the particle size of agglomerated particles existing in the slurry.

In this regard, it is to be noted that, from the view point of enhancing the strength of the obtained powder, it is preferred that the duration of agitation at the third agitation power is controlled such that agglomerated particles in the slurry have very small particle sizes with respect to the particle size of the powder to be manufactured (that is, a target particle size of the powder).

Specifically, it is preferred that the particle size distribution of agglomerated particles of hydroxyapatite existing in the slurry, that is the ratio of agglomerated particles having a specific particle size to the total of the agglomerated particles existing in the slurry is adjusted so as to satisfy the following conditions.

<1> The ratio of agglomerated particles having a particle size of one-half of or less than a target particle size of the powder to the total of the agglomerated particles existing in the slurry is 55% or more, and preferably 60% or more.

<2> Agglomerated particles having a particle size of one-thirds of or less than a target particle size of the powder occupy the largest percentage of the total of the agglomerated particles existing in the slurry.

It is to be noted here that, in the present invention, it is preferable that at least one of the conditions <1> and <2> described above is satisfied, and more preferable that both the conditions are satisfied. This enables the strength of the obtained powder to be further enhanced.

In a case that the produced synthetic material is hydroxyapatite, the conditions <1> and <2> are preferably applied when a target particle size of the powder is set to be about 10 to 80 µm, especially about 15 to 43 µm.

Also, in a case that the produced synthetic material is hydroxyapatite, when the ratio of agglomerated particles having a particle size of 13.0 to 18.5 µm is defined as A, and the ratio of agglomerated particles having a particle size of 3.27 to 5.50 µm is defined as B, it is preferable that A and B are adjusted so as to satisfy the formula of B/A>2, and more preferable that they are adjusted so as to satisfy the formula of B/A>3. This enables the strength of the powder of hydroxyapatite to be further enhanced.

When at least one of the conditions <1> and <2> described above is satisfied, the step S13 (S1) is completed and then the manufacturing process proceeds to the next step S2. As described above, the duration of agitation at the third agitation power is determined based on the particle size distribution of agglomerated particles existing in the slurry. In particular, in a case that the produced synthetic material is hydroxyapatite, the duration of agitation at the third agitation power is determined based on the ratio between the agglomerated particles having a particle size of 13.0 to 18.5 µm and the agglomerated particles having a particle size of 3.27 to 5.50 µm. This enables the duration of agitation at the third agitation power to be more precisely determined and, as a result, it is possible to more precisely adjust the strength of the obtained powder to one desired.

It is to be noted that the particle size of agglomerated particles can be measured based on a sampled slurry using a particle size analyzer.

As described above, in the present embodiment, the particle size of agglomerated particles is adjusted by temporarily decreasing the agitation power for the slurry to a relatively low level (second agitation power) and then increasing the agitation power again to a relatively high level (third agitation power). Namely, the particle size of agglomerated particles is adjusted by producing agglomerated particles having relatively large particle sizes and then breaking them into small ones. According to this method, it is possible to more efficiently adjust the particle size of agglomerated particles to one desired in a relatively shorter duration of agitation, as compared to a case that the particle size of agglomerated particles is adjusted without the agitation power for the slurry being changed (that is, with the agitation power for the slurry being maintained constant).

<S2: Step of Drying Slurry to Obtain Powder of Hydroxyapatite>

In this step, the slurry prepared in the step S1 is dried to obtain a powder.

A spray-dry method is preferably used for this purpose, because it enables a powder having a desired particle size to be reliably obtained in a short period of time.

The particle size of the manufactured powder (that is a target particle size of the powder) is not limited to any specific value, but is preferably about 3 to 300 µm, and more preferably about 10 to 120 µm.

In this regard, it is to be noted that the manufacturing method of a powder of the present embodiment is especially suitable for manufacturing a powder of which a target particle size is about 10 to 80 µm, especially about 15 to 43 µm.

Through the steps described above, a powder of hydroxyapatite (synthetic material) is manufactured.

The thus manufactured hydroxyapatite powder is sintered, and the sintered powder is suitably used as a stationary phase or the like for chromatography.

Also, such a hydroxyapatite powder is preferably used as a biomaterial for various medical or dental articles such as artificial bones, a spacer for use in the treatment of vertebral arch, an auditory ossicle, and dental implants and the like. In this case, the hydroxyapatite powder is formed into a desired shape to prepare a green body, and the green body is then sintered to obtain such articles.

Although the manufacturing method of a powder of the present invention has been described as above, the present invention is not limited thereto.

For example, the present invention may further include a desired pre-treatment process prior to the step S1, a desired intermediate-treatment process between the step S1 and the step S2, or a desired after-treatment process after the step S2.

Further, in the present embodiment described above, the particle size of agglomerated particles of the synthetic material existing in the slurry is adjusted for the purpose of enhancing the strength of the obtained powder. However, the purpose of the particle size adjustment of the present invention is not limited thereto.

For example, it is possible to obtain a powder having a desired strength by appropriately adjusting the particle size of agglomerated particles of the synthetic material existing in the slurry according to a target particle size of the powder. Specifically, in a case that the synthetic material is hydroxyapatite, appropriate adjustment of a value of the B/A described above within the range of 0.5 to 4.5 enables powders having desired strength in a range from a relatively low to a relatively high level to be obtained.

EXAMPLE

Next, a description will be made with regard to actual examples of the present invention.

Example 1

In Example 1, a hydroxyapatite powder was manufactured, which can be used as a material of a sintered body used for an artificial bone.

It is to be noted here that, in Example 1, the particle size of agglomerated particles existing in a slurry was adjusted for a purpose of manufacturing a powder having high strength, because the artificial bone requires to have high strength.

Further, in Example 1, a target particle size of the hydroxyapatite powder (that is the particle size of the manufactured powder) was set to be 18 μm.

Example 1A

First, 140 g of calcium hydroxide was dispersed in 1,200 ml of pure water, and it was placed in a beaker. Then, 700 ml of aqueous solution of phosphoric acid (in which the concentration of phosphoric acid was 10 wt %) was dropped into the calcium hydroxide-dispersed pure water in the beaker under agitation at a first agitation power, to thereby obtain a slurry. It is to be noted here that the first agitation power at this time was set to be an output of 1.3 W for 1 L of the slurry.

Here, as the dropping of the aqueous solution of phosphoric acid proceeded, the viscosity of the slurry was increased. Then, at the time when the pH value of the slurry reached the vicinity of 9.8 (that is the isoelectric point of hydroxyapatite), the viscosity of the slurry sharply rose to approach its maximum (peak) value.

At this timing, that is, at the time when the viscosity of the slurry approached its maximum value, the agitation power for the slurry was lowered from the first agitation power to a second agitation power.

In this regard, it is to be noted that the second agitation power at this time was set to be an output of 0.37 W (that is an output of about 28% of the output of the first agitation power) for 1 L of the slurry.

After the determination that synthesis of hydroxyapatite was completed, the agitation power for the slurry was increased from the second agitation power to a third agitation power.

In this regard, it is to be noted that the third agitation power at this time was set to be an output of 1.1 W (that is an output of about 297% of the output of the second agitation power) for 1 L of the slurry.

The agitation of the slurry at the third agitation power was continued for 0.5 hour with checking of the particle size distribution of agglomerated particles of hydroxyapatite existing in the slurry.

In Table 1 below, the ratio of agglomerated particles of hydroxyapatite having a particle size of 3.27 to 5.50 μm and the ratio of agglomerated particles of hydroxyapatite having a particle size of 13.0 to 18.5 μm, to the total of the agglomerated particles existing in the slurry at the time when the agitation of the slurry at the third agitation power was completed are shown.

The slurry was then spray-dried to obtain a hydroxyapatite powder. The average particle size of the obtained hydroxyapatite powder was about 18 μm.

The thus obtained hydroxyapatite powder was pre-sintered under atmospheric pressure at a temperature of 750° c. for 4 hours, and was then ground using a grinder (which has an output of 11 kW), to thereby obtain a secondary hydroxyapatite powder.

Next, 2,000 g of aqueous solution of methyl cellulose (1 wt %) was added to 1,000 g of the secondary hydroxyapatite powder, and they were mixed to prepare a paste containing bubbles.

The paste was filled into a forming die having a predetermined shape, and was air-dried, to thereby obtain a green body.

Next, the green body was sintered under atmospheric pressure at a temperature of 1,200° c. for 4 hours, to thereby obtain a sintered body. 100 sintered bodies were manufactured in Example 1A.

Example 1B

In Example 1B, a hydroxyapatite powder was manufactured in the same manner as Example 1A except that the duration of agitation at the third agitation power was set at 9 hours. 100 sintered bodies were then manufactured in the same manner as Example 1A using the thus obtained hydroxyapatite powder.

Example 1C

In Example 1C, a hydroxyapatite powder was manufactured in the same manner as Example 1A except that the duration of agitation at the third agitation power was set at 72 hours. 100 sintered bodies were then manufactured in the same manner as Example 1A using the thus obtained hydroxyapatite powder.

<Evaluation>

For each of the sintered bodies manufactured in Examples 1A to 1C, measurement of porosity was performed. Sintered bodies having a porosity of 45±3% were regarded as accepted products.

The measurement results of porosity and conditions in manufacturing a hydroxyapatite powder in Examples 1A to 1C are shown in Table 1.

TABLE 1

(Example 1)

| | First Agitation Power Output[W]/ 1 L of slurry | Second Agitation Power Output[W]/ 1 L of slurry | Third Agitation Power Output[W]/ 1 L of slurry | Ratio of agglomerated particles having a specific particle size which exist in slurry [%] | | Particle size of agglomerated particles which occupy the largest percentage in slurry [μm] | Sintered Body Number of Accepted Products |
|---|---|---|---|---|---|---|---|
| | | | | Particle size of 3.27 to 5.50 μm Particle size of 13.0 to 18.5 μm | Particle size of one-half of or less than a target particle size of powder | | |
| Example 1A | 1.3 | 0.37 | 1.1 | 12.09<br>20.51 | 22.90 | 15.56 | 84 |
| Example 1B | 1.3 | 0.37 | 1.1 | 21.36<br>15.83 | 41.03 | 13.08 | 92 |
| Example 1C | 1.3 | 0.37 | 1.1 | 41.55<br>9.68 | 62.82 | 4.62 | 99 |

As shown in Table 1, almost all of the sintered bodies manufactured in Examples 1A to 1C had the desired porosity.

This result shows that each of the hydroxyapatite powders manufactured in Examples 1A to 1C had sufficient particle strength so that the pre-sintered powder was not excessively fragmented when ground, and thus a manufactured sintered body was appropriately prevented from being made excessively dense.

Namely, it is clear that a sintered body having a desired porosity can be reliably obtained by using any one of the hydroxyapatite powders manufactured in Examples 1A to 1C.

In addition, all of the sintered bodies manufactured in Examples 1A to 1C had sufficient strength.

From the results described above, it is clear that all of the sintered bodies manufactured in Examples 1A to 1C had appropriate qualities that can be used for artificial bones.

Example 2

In Example 2, a hydroxyapatite powder which can be used as a stationary phase material for chromatography was manufactured.

It is to be noted here that in Example 2 the particle size of agglomerated particles existing in a slurry was adjusted for the purpose of manufacturing a powder having high strength so that a stationary phase for use in chromatography does not collapse when filled in a column, since a stationary phase for chromatography requires to have high strength.

Further, in Example 2, a target particle size of the hydroxyapatite powder (that is the particle size of the manufactured powder) was set to be 40 μm.

Examples 2A to 2C

In each of Examples 2A to 2C, a hydroxyapatite powder was manufactured in the same manner as Example 1A, with the exception of the conditions shown in Table 2.

In this regard, it is to be noted that the duration of agitation at the third agitation power was set at 1 hour, 11 hours, and 72 hours in Example 2A, Example 2B, and Example 2C, respectively. An output of the third agitation power was set at 1.3 W for 1 L of the slurry.

Next, each of the thus-obtained hydroxyapatite powders was classified using an air classifier to obtain a hydroxyapatite powder having an average particle size of 40 μm and a sharp particle size distribution.

Such a hydroxyapatite powder was sintered under atmospheric pressure at a temperature of 400° c. for 4 hours, to thereby obtain a sintered powder.

<Evaluation>

For each of the sintered powders manufactured in Examples 2A to 2C, measurement of compression strength was performed.

It is to be noted here that the measurement was performed using a micro compression testing machine (manufactured by Shimadzu Corporation, product code MCT-500).

The compression strength measurement results and conditions in manufacturing a hydroxyapatite powder in each of Examples 2A to 2C are shown in Table 2.

TABLE 2

(Example 2)

| | First Agitation Power Output[W]/ 1 L of slurry | Second Agitation Power Output[W]/ 1 L of slurry | Third Agitation Power Output[W]/ 1 L of slurry | Ratio of agglomerated particles having a specific particle size which exist in slurry [%] | | Particle size of agglomerated particles which occupy the largest percentage in slurry [μm] | Sintered Powder Compression Strength [MPa] |
|---|---|---|---|---|---|---|---|
| | | | | Particle size of 3.27 to 5.50 μm Particle size of 13.0 to 18.5 μm | Particle size of one-half of or less than a target particle size of powder | | |
| Example 2A | 1.3 | 0.37 | 1.3 | 12.94<br>18.77 | 57.42 | 15.56 | 1.980 |
| Example 2B | 1.3 | 0.37 | 1.3 | 21.78<br>15.15 | 61.86 | 4.62 | 2.191 |
| Example 2C | 1.3 | 0.37 | 1.3 | 37.00<br>11.05 | 78.16 | 4.62 | 3.410 |

As shown in Table 2, each of the sintered powders manufactured in Examples 2A to 2C had extremely high compression strength.

The compression strength of the sintered powder demonstrated a tendency to increase in proportion to the duration of agitation at the third agitation power.

In addition, it was confirmed that there is no difference among the sintered powders manufactured in Examples 2A to 2C in their initial properties such as specific surface area which affect on adsorption and separation abilities that are required for a stationary phase for use in chromatography.

From the results described above, it is clear that each of the sintered powders manufactured in Examples 2A to 2C had excellent durability and appropriate qualities that can be used for a stationary phase for use in chromatography.

As is apparent from the above descriptions, according to the present invention, in the step of preparing a slurry containing a synthetic material such as a calcium phosphate-based compound, by adjusting the particle size of agglomerated particles of the synthetic material existing in the slurry, it is possible to adjust the strength of the obtained powder.

Further, it is also possible to more reliably adjust the strength of the obtained powder by appropriately setting a control sequence of agitation power.

In particular, by controlling agitation power such that agglomerated particles of the synthetic material existing in the slurry have small particle sizes, it is possible to obtain a powder having satisfactorily high strength.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2002-004596 (filed on Jan. 11, 2002) which is expressly incorporated herein by reference in its entireties.

What is claimed is:

1. A method of manufacturing a powder, comprising:
preparing a slurry containing agglomerated particles of a synthetic material which is produced by reacting a first material and a second material under agitation; and
drying the slurry to obtain a powder of the synthetic material, wherein the particle size of the agglomerated particles is adjusted by changing an agitation power for agitating the slurry in the process of reacting the first material and the second material to prepare the slurry.

2. The method of manufacturing a powder as claimed in claim 1, wherein the agitation power is changed on the basis of a change in the viscosity of the slurry and/or a change in the pH value of the slurry.

3. The method of manufacturing a powder as claimed in claim 2, wherein the agitation power includes at least a first agitation power and a second agitation power which is lower than the first agitation power.

4. The method of manufacturing a powder as claimed in claim 3, wherein the agitation power further includes a third agitation power which is larger than the second agitation power, in which the control of the agitation power is carried out so that the slurry is agitated at the third agitation power before or after the reaction of the first material and the second material is completed.

5. The method of manufacturing a powder as claimed in claim 4, wherein the third agitation power is an output of 0.75 to 2 W for 1 L of the slurry.

6. The method of manufacturing a powder as claimed in claim 4, wherein a duration of agitation at the third agitation power is determined on the basis of a particle size distribution of the agglomerated particles.

7. The method of manufacturing a powder as claimed in claim 6, wherein the duration of agitation at the third agitation power is controlled so that the ratio of agglomerated particles having a particle size of one-half of or less than a target particle size of the powder to the total of the agglomerated particles existing in the slurry is 55% or more.

8. The method of manufacturing a powder as claimed in claim 6, wherein the duration of agitation at the third agitation power is controlled so that agglomerated particles having a particle size of one-thirds of or less than a target particle size of the powder occupy the largest percentage of the total of the agglomerated particles existing in the slurry.

9. The method of manufacturing a powder as claimed in claim 1, wherein at least one of the first material and the second material is in a solution form.

10. The method of manufacturing a powder as claimed in claim 1, wherein the synthetic material is a ceramic material.

11. The method of manufacturing a powder as claimed in claim 1, wherein the synthetic material is a calcium phosphate-based compound.

12. The method of manufacturing a powder as claimed in claim 1, wherein the first material, the second material and the synthetic material are calcium hydroxide, phosphoric acid and hydroxyapatite, respectively.

13. The method of manufacturing a powder as claimed in claim 12, wherein the completion of the reaction of the calcium hydroxide and the phosphoric acid is determined by detecting an amount of a substance other than the hydroxyapatite existing in the slurry.

14. The method of manufacturing a powder as claimed in claim 13, wherein the substance is calcium hydroxide or tricalcium phosphate.

15. The method of manufacturing a powder as claimed in claim 4, wherein the first material, the second material and the synthetic material are calcium hydroxide, phosphoric acid and hydroxyapatite, respectively.

16. The method of manufacturing a powder as claimed in claim 15, wherein a target particle size of the powder is set to be 15 to 43 μm, in which the duration of agitation at the third agitation power is controlled so that the ratio of agglomerated particles having a particle size of one-half of or less than a target particle size of the powder to the total of the agglomerated particles existing in the slurry is 55% or more.

17. The method of manufacturing a powder as claimed in claim 15, wherein a target particle size of the powder is set to be 15 to 43 μm, in which the duration of agitation at the third agitation power is controlled so that agglomerated particles having a particle size of one-thirds of or less than a target particle size of the powder occupy the largest percentage of the total of the agglomerated particles existing in the slurry.

18. The method of manufacturing a powder as claimed in claim 15, wherein when the ratio of agglomerated particles having a particle size of 13.0 to 18.5 μm is defined as A, and the ratio of agglomerated particles having a particle size of 3.27 to 5.50 μm is defined as B, the duration of agitation at the third agitation power is controlled based on the ratio between the A and B.

19. The method of manufacturing a powder as claimed in claim 18, wherein the duration of agitation at the third agitation power is controlled so that the ratio between the A and B satisfies the formula of B/A>2.

20. A method of manufacturing a powder, comprising:

preparing a slurry containing agglomerated particles of a synthetic material which is produced by reacting a first material and a second material under agitation; and drying the slurry to obtain a powder of the synthetic material, wherein the particle size of the agglomerated particles is adjusted by, in the preparing the slurry, controlling an agitation power for agitating the slurry;

the agitation power is controlled on the basis of a change in the viscosity of the slurry;

the agitation power includes at least a first agitation power and a second agitation power which is lower than the first agitation power; and the control of the agitation power is carried out so that the slurry is initially agitated at the first agitation power, and at the time when the viscosity of the slurry approaches its maximum value, the slurry is agitated at the second agitation power.

21. The method of manufacturing a powder as claimed in claim 20, wherein the first agitation power is an output of 0.75 to 2 W for 1 L of the slurry.

22. The method of manufacturing a powder as claimed in claim 20, wherein the second agitation power is an output of 0.27 to 0.7 W for 1 L of the slurry.

23. A method of manufacturing a powder, comprising:

preparing a slurry containing agglomerated particles of a synthetic material which is produced by reacting a first material and a second material under agitation; and drying the slurry to obtain a powder of the synthetic material, wherein the particle size of the agglomerated particles is adjusted by, in the preparing the slurry, controlling an agitation power for agitating the slurry;

the agitation power is controlled on the basis of a change in the pH value of the slurry;

the agitation power includes at least a first agitation power and a second agitation power which is lower than the first agitation power; and the control of the agitation power is carried out so that the slurry is initially agitated at the first agitation power, and at the time when the pH value of the slurry reaches the vicinity of the isoelectric point of the synthetic material, the slurry is agitated at the second agitation power.

24. The method of manufacturing a powder as claimed in claim 23, wherein the first agitation power is an output of 0.75 to 2 W for 1 L of the slurry.

25. The method of manufacturing a powder as claimed in claim 23, wherein the second agitation power is an output of 0.27 to 0.7 W for 1 L of the slurry.

* * * * *